United States Patent [19]

Blom et al.

[11] Patent Number: 4,586,931
[45] Date of Patent: May 6, 1986

[54] AUTO ACTUATABLE SWITCH, SPEECH SIMULATOR AND METHOD FOR TRACHEOTOMIZED INDIVIDUALS

[75] Inventors: Eric D. Blom; Mark I. Singer; Barry A. Harkleroad, all of Indianapolis, Ind.

[73] Assignee: Hansa Medical Products, Inc., Indianapolis, Ind.

[21] Appl. No.: 617,702

[22] Filed: Jun. 5, 1984

Related U.S. Application Data

[62] Division of Ser. No. 329,768, Dec. 11, 1981, abandoned.

[51] Int. Cl.[4] ............................................... A61F 2/20
[52] U.S. Cl. ....................................................... 623/9
[58] Field of Search ............... 340/551, 573, 407, 579; 280/292 WC, 289 WC; 180/DIG. 907; 128/639, 640, 733, 739, 774, 782, 207.16, 207.15, 207.18; 3/1.1, 1.2, 1.3; 623/9; 381/70

[56] References Cited

U.S. PATENT DOCUMENTS

| 1,867,350 | 7/1932 | Burchett | 623/9 |
| 1,910,966 | 5/1933 | Riesz et al. | 623/9 |
| 4,178,938 | 12/1979 | Au | 128/207.15 |
| 4,292,472 | 9/1981 | Lennox | 623/9 |
| 4,298,863 | 11/1981 | Natitus et al. | 340/573 |
| 4,338,488 | 7/1982 | Lennox | 381/70 |
| 4,489,440 | 12/1984 | Chaoui | 623/9 |

FOREIGN PATENT DOCUMENTS 1248230  8/1967  Fed. Rep. of Germany ..................... 128/207.15

OTHER PUBLICATIONS

Blue Line Tracheostomy Tubes, Portex, Inc.
"Specking Cuffed Tracheostomy Tube", Peter Safar, MD; Ake Grenvik, MD, Critical Care Medicine, vol. 3, No. 1, Jan.-Feb., 1975.
7. The Artificial Larynx: Past and Present, Eric D. Blom, Ph.D., pp. 57-66.

Primary Examiner—Richard J. Apley
Assistant Examiner—James Prizant
Attorney, Agent, or Firm—Barnes & Thornburg

[57] ABSTRACT

A method for simulating speech in a tracheotomized individual includes providing a source of compressed air, regulating the air pressure, and controlling the flow of air from the source between a condition in which airflow is stopped and a condition in which airflow is allowed in response to actuation by the individual. The air flow is supplied to a reed to vibrate it, and the resulting vibration-modulated air flow is introduced into the pharynx of the individual, permitting the individual to articulate audibly comprehensible speech. Apparatus for carrying out this method is also described.

40 Claims, 6 Drawing Figures

AUTO ACTUATABLE SWITCH, SPEECH SIMULATOR AND METHOD FOR TRACHEOTOMIZED INDIVIDUALS

This is a division of application Ser. No. 329,768 filed Dec. 11, 1981, now abandoned.

BACKGROUND OF THE INVENTION

The subject matter of the invention relates to a speech simulator, auto actuatable switch therefore, and a method for simulating speech in tracheotomized patients, including quadriplegics.

The patient dependent on mechanical ventilation through a tracheostomy is unable to vocalize because of interrupted air flow to the larynx. An inability to communicate may compromise medical care and prove a source of extreme frustration and emotional stress to the patient. It is generally not feasible to disconnect the ventilator, deflate the cuff on the tracheostomy tube and occlude the tube to momentarily allow the patient to exhale around it for brief communication. Moreover, should the patient be a quadriplegic, written and gestural communications are impossible and lip reading or an elimination process of questioning both have their obvious limitations.

Electronic artificial larynges have been developed to provide rudimentary communication for tracheotomized patients. The most common artificial larynx is generally a hand held, battery powered instrument which emits a continuous high frequency buzz. The buzzing sound is transmitted through the neck into the mouth where it is modified by mouth and throat movements to produce recognizable speech like sounds. Difficulty is often encountered however, in placing the instrument effectively and securely against the skin of the mandibular triangle and coordinating sound production with speech articulation. Importantly, the quadriplegic patient remains dependent on others to anticipate when he wants to speak and to operate the artificial larynx.

Pneumatic artifical larynges have also been developed. The most common of these devices is the Tokyo artificial larynx which has a stoma cover connected to a mouth tube with a vibrator chamber therebetween. A modified version has a finger-controlled breathing port by the vibrator chamber. Both of these devices are hand-held and manually operable.

The obvious limitations inherent in the use of the artificial larynx by a tracheotomized quadriplegic led to the development of an auto actuatable device comprising a headband with an adjustable sliding arm which actuates a tone generator, the output of which is tubed to a patient's mouth. A sliding contact switch mounted on the forehead is utilized to activate the tone generator to produce sound for speech by the simple wrinkling action of the patient's forehead. This device has a major limitation in that the headband must be adjusted snuggly enough to stay in place, but not so tight as to restrict circulation. This often necessitates the use of a cotton sweatband or a light weight cap to increase comfort and to decrease skin irritation and slipping on oily skin or hair. Moreover, the location of the tube within the patient's mouth interferes significantly with the patient's ability to articulate. The opening to the mouth tube frequently fouls with saliva thus impeding speech production. Additionally, speech produced by this device is electronic sounding and this artificial quality is frequently rejected by potential users.

Alternative devices have also included the Pitt "Speaking Tracheostomy Tube" and the Portex "Trach Talk" which comprise tracheostomy tubes having a narrow gauge conduit incorporated into their convex surface that terminates at a fenestration slightly above the inflatable cuff. An external air flow can be delivered to the larynx through this conduit independent of the oxygen being supplied to the lungs by mechanical ventilation. This is accomplished manually by the patient occluding a "Y" connector attached between the narrow gauge conduit and a source of compressed air. In so doing, sufficient air flow is provided the patient such that an audible whisper might be produced.

In practice, it has been found that the location of a fenestration through which compressed air is delivered to the larynx is situated too close to the tracheostomy, thereby allowing air to escape out and around the tracheostomy tube. This results in decreased air flow for speech and an annoying hissing noise at the neck. Furthermore, patients have frequently reported that air flow reaching the larynx tickles or gags them if for example, the flow is directed in too narrow a stream. It has been shown that patients on a ventilator frequently have laryngeal and supra-laryngeal tissue changes secondary to traumatic intubation. In many instances these tissue changes interfere with adequate air flow for voice production in patients with whom the "talking trach tubes" are tried. Finally, and most importantly, quadriplegic patients who can achieve audible speech with currently available speaking tracheostomy tubes still remain dependent on others to anticipate when they want to speak and to operate an external air flow.

It would therefore be highly desirable to provide an improved speech simulator and a method for simulating speech for tracheotomized patients.

It would also be highly desirable to provide an improved auto actuatable speech simulator and method which allows oral communication with, and readily intelligible speech by, a tracheotomized patient.

It would also be highly desirable to provide an improved auto actuatable speech simulator and method which allows oral communication with, and readily intelligible speech by, a tracheotomized quadriplegic patient.

It would be further highly desirable to provide an improved auto actuatable speech simulator and method which can be switched on and off by hand, if possible, or by an improved forehead mounted switch by quadriplegic patients.

It would be further highly desirable to provide an improved speech simulator and method which provides for the introduction of air through a nasal catheter which does not bother the patient, interfere with the patient's speech or produce unwanted noises or physical sensations during use.

It would be further highly desirable to provide an improved speech simulator and method which provides for a non-electronic, more natural sounding simulated speech by a tracheotomized patient.

It would be further highly desirable to provide an improved speech simulator and method which provides a device which may be simply and inexpensively produced.

It would be further highly desirable to provide an improved speech simulator and method which requires no assistance and, little, if any, instruction of the tracheotomized patient to operate.

It would be still further highly desirable to provide an improved speech simulator and an auto actuatable switch therefore which can be used by a quadriplegic or even the most severely paralyzed patient.

It still further highly desirable to provide an improved auto actuatable switch for use by a quadriplegic which has no moving parts and is comfortable to wear.

It would finally be highly desirable to provide an improved auto actuatable switch for use by a quadriplegic which is simple to use, and may be utilized to operate any electrically actuatable device.

SUMMARY OF THE INVENTION

It is therefore a primary object of the invention to provide an improved speech simulator and method of simulating speech by a tracheotomized patient.

It is another object of the invention to provide an improved auto actuatable speech simulator and method which allows oral communication with, and readily intelligible speech by, a tracheotomized patient.

It is another object of the invention to provide an improved auto actuatable speech simulator and method which allows oral communication with, and readily intelligible speech by, a tracheotomized quadriplegic patient.

It is another object of the invention to provide an improved auto actuatable speech simulator and method which can be switched on and off by hand, if possible, or by an improved forehead mounted switch by quadriplegic patients.

It is another object of the invention to provide an improved speech simulator and method which provides for the introduction of air through a nasal catheter which does not bother the patient, interfere with the patient's speech, or produce unwanted noises or physical sensations during use.

It is another object of the invention to provide an improved speech simulator and method which provides for a non-electronic, more natural sounding simulated speech by a tracheotomized patient.

It is another object of the invention to provide an improved speech simulator and method which provides a device which may be simply and inexpensively produced.

It is another object of the invention to provide an improved speech simulator and method which requires no assistance and, little, if any, instruction of the tracheotomized patient to operate.

It is another object of the invention to provide an improved speech simulator and an auto actuatable switch therefore which can be used by a quadriplegic or even the most severely paralyzed patient.

It is further an object of the invention to provide an improved auto actuatable switch for use by a quadriplegic which has no moving parts and is comfortable to wear.

It is further an object of the invention to provide an improved auto actuatable switch for use by a quadriplegic which is simple to use, and may be utilized to operate any electrically actuatable device.

Finally, it is an object of the invention to provide an improved speech simulator method and auto actuatable switch which meet all of the aforementioned objects, respectively.

Briefly, what is provided is a speech simulator for tracheotomized individuals comprising a source of pressurized air, a regulator governing the pressure of the air, and a valve responsive to actuation by an individual interconnected between the air source and the regulator. The valve is operable between a first position thereof wherein the air from the source is stopped and a second position thereof wherein the air passes through the valve. A flexible tube ducts the air through the regulator to a reed device. The reed device vibrates audibly in response to the passage of the air through the valve and past the reed. A catheter having a proximal reed end and a distal pharyngeal end is introduced through a nostril into the pharynx of an individual. The catheter introduces air from the valve and reed into the pharynx of an individual, whereby the individual may articulate audibly comprehensible speech. A switch for actuation of the simulator by a individual comprises first and second adhesive pads for affixation to an epidermal area of a quadriplegic individual at a first displaced distance and movable towards each other to a relatively lesser second displaced distance by voluntary muscular action of the individual. A field producing device is secured to the first adhesive pad and a field responsive switch is secured to the second adhesive pad. The switch has an open condition thereof when the adhesive pads are at a first displaced distance and a closed condition thereof when the adhesive pads are at a second and more proximal displaced distance. A method for simulating speech in a tracheotomized individual comprising the steps of supplying a source of pressurized air, controlling the flow of the air between a first condition thereof wherein flow of the air is stopped and a second condition thereof wherein the air is allowed to flow by a switch responsive to actuation by an individual. The pressure of the air is governed by a regulator and the air is ducted from the switch to a reed and the reed is allowed to vibrate audibly in response to the passage of the air past the reed. The air past the reed is introduced into the pharynx of an individual through a catheter inserted through a nostril whereby the individual may articulate audibly comprehensible speech. A method for auto actuation of a switch by a quadriplegic individual comprising the steps of affixing first and second adhesive pads to an epidermal area of a quadriplegic individual at a first displaced distance. The first and second adhesive pads are moved to a relatively lesser displaced distance thereof by voluntary muscular action of the quadriplegic individual. A field producing device is secured to the first pad and a field responsive switch is attached to the second adhesive pad having an open condition thereof when the adhesive pads are first displaced distance and a closed position thereof when the adhesive pads are at the second and more proximal displaced distance.

BRIEF DESCRIPTION OF THE DRAWINGS

The above-mentioned and other features and objects of this invention and the manner of attaining them will become more apparent and the invention itself will be best understood by reference to the following description of an embodiment of the invention taken in conjunction with the accompanying drawings, wherein.

DESCRIPTION OF A SPECIFIC EMBODIMENT

Figure 1:
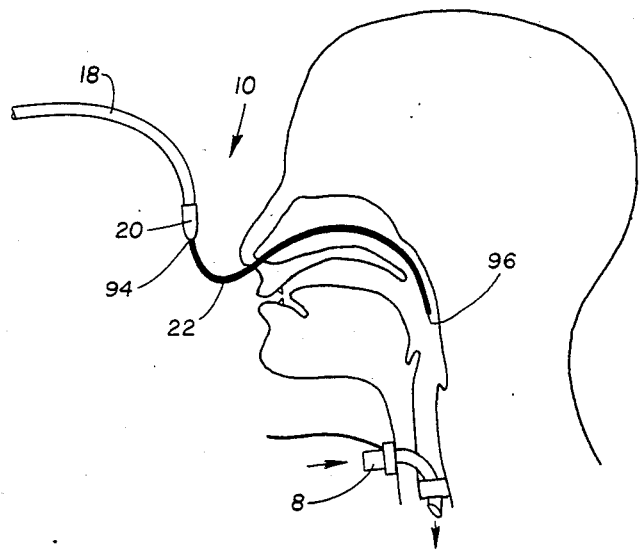
FIG. 1 is a diagrammatic representation of a tracheotomized patient illustrating the insertion of a cuffed tracheostomy tube and the tubing, reed housing and catheter of the invention.

Referring to the drawings, the improved auto actuable speech simulator 10 of the invention is shown to comprise a compressed air source 12, an air valve 16 and an air pressure regulator 14. Air source 12 furnishes air under pressure through air valve 16 to regulator 14. Regulator 14 conducts air through tubing 18 into reed housing 20 and past reed 98 located in reed chamber 102 to produce vibrating air which is conducted out of the reed chamber 102 through catheter 22 into the pharynx of a tracheotomized patient having a trachostomy tube 8 to provide patient ventilation.

Figure 2:
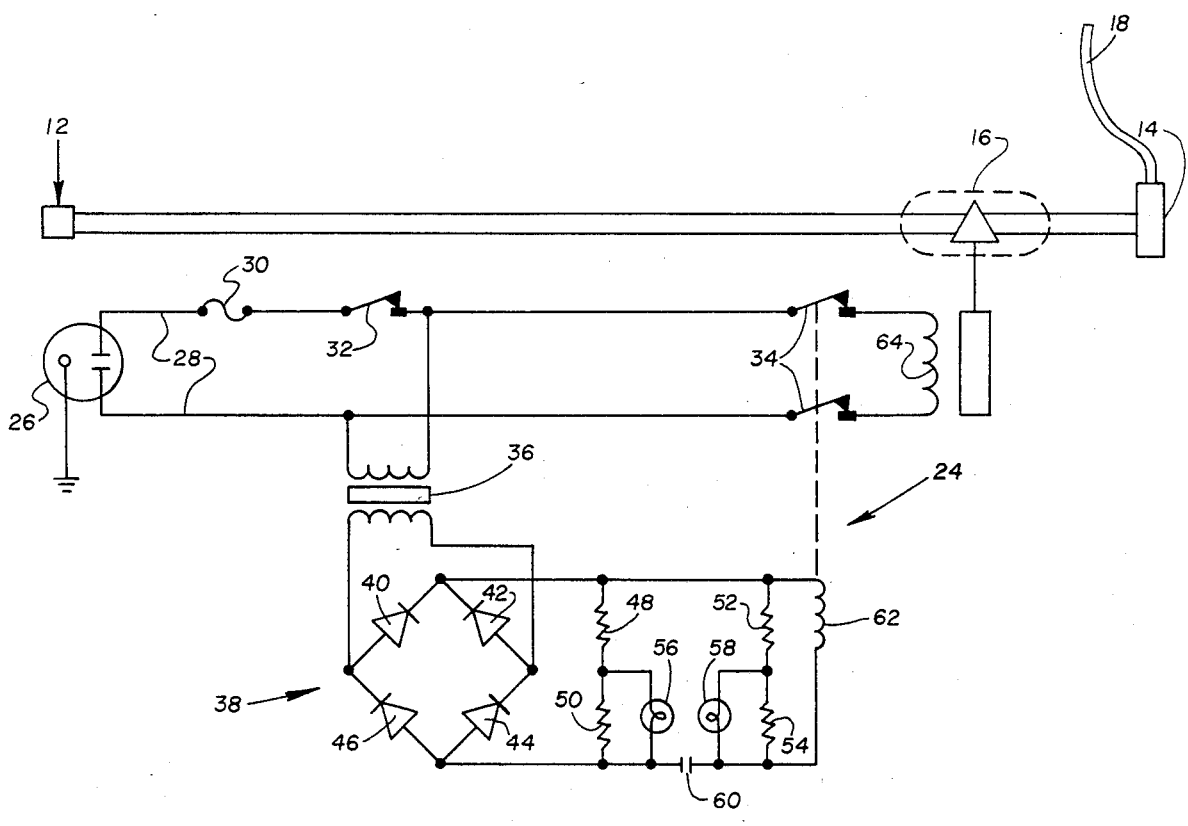
FIG. 2 is a schematic illustration of the air valve and power supply of the invention showing the electrical circuitry thereof.

Since vibrating air is delivered to the pharynx of a tracheotomized individual at a relatively low pressure, compressed air source 12 can be one of any number of commercially available compressed air sources. In most specific embodiments, however, the compressed air source 12 is either the readily available compressed air source in patient rooms as found in many hospitals and doctors offices or portable cylinders of compressed air. In specific embodiments, such air sources furnish air at pressures in the range of from about 40 psi to about 90 psi. As shown in FIG. 2, air source 12 is connected through valve 16 to regulator 14. Regulator 14, in specific embodiments, may be any commercially available air pressure regulator. When air source 12 is either in the form of available patient room air sources or portable compressed air cylinders, regulator 14 may be one of any of the commercially available air regulators used in conjunction with such compressed air sources for other patient purposes. In many specific embodiments, air source 12 and regulator 14 are associated therewith a humidifier (not shown) to humidify the air prior to its entry into air regulator 14. Moisturized air reduces the drying of the membranes in the pharynx by use of the invention.

Tubing 18 can be any flexible tubing having a wall thickness sufficiently able to withstand the air pressure of air source 12 and to prevent kinking or sidewall collapse during use. Preferred tubing 18 suffers no collapse or kinking when bent into a radius as small as about one-half inch. In a specific embodiment, tubing 18 can be of metal reinforced elastomeric materials, i.e. silastic and latex materials. Tubing 18 must be long enough and flexible enough to provide for sufficient patient mobility. In a specific embodiment, tubing 18 is TYGON tubing having an one-eighth inch internal diameter such as normally used in hospital room in connection with patient room air sources.

Figure 5:
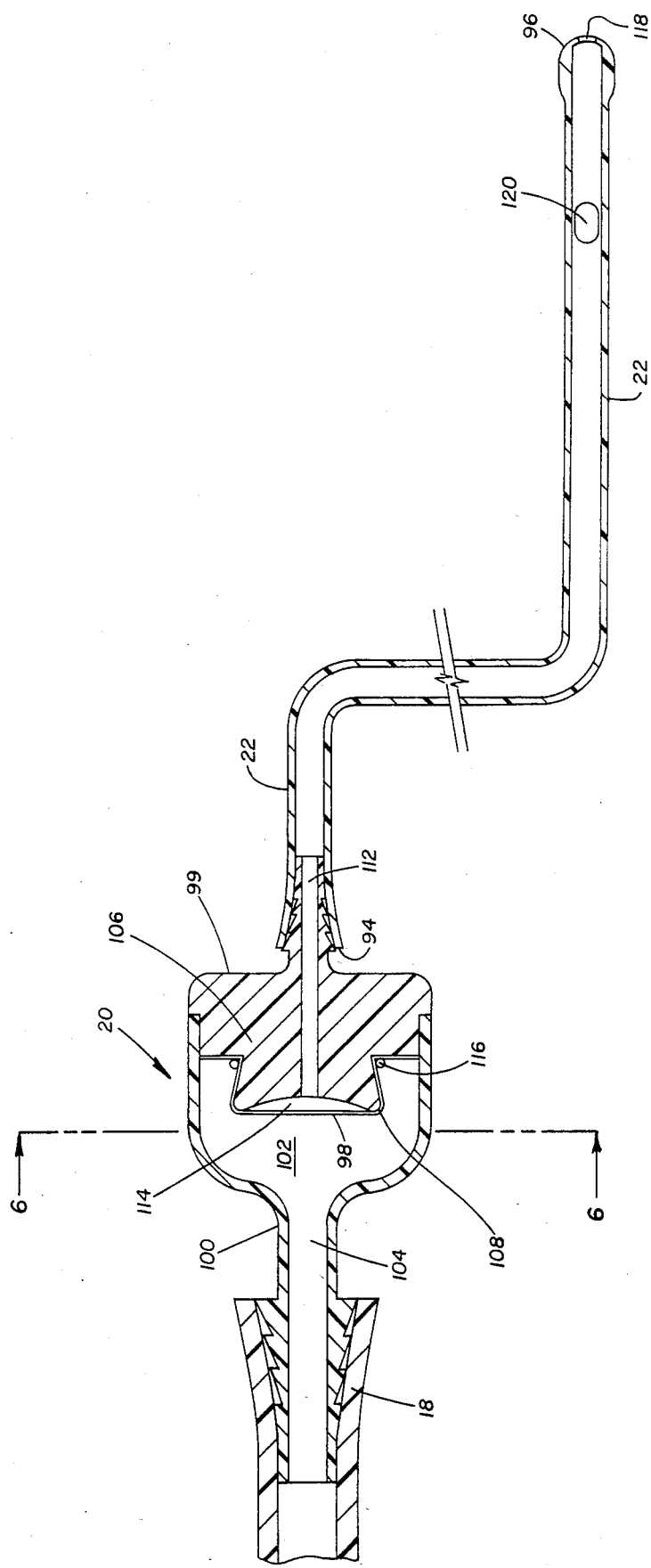
FIG. 5 is a closeup perspective, partially broken away, and fragmentary view of the tubing, reed housing and catheter shown in FIG. 1.

Referring to FIG. 5, reed housing 20, tubing 18 and catheter 22 are shown in detail. Housing 20 has opposite ends 99 and 100 and an interior chamber 102. A pressurized air duct 104 is secured to housing 20 at end 100 and extends into chamber 102. Pressurized air duct 104 is attached to tubing 18 as shown in FIG. 1. Adjacent to end 99 of reed housing 20 is an air outlet 112. A reed support 106 is secured to reed housing 20 at end 100 and extends inwardly of chamber 102. Reed support 106 surrounds pressurized air outlet 112. Reed support 106 has reed supporting surfaces 108 thereon which are spaced from both air pressurized duct 104 and air outlet 112. Reed supporting surfaces 108 face opposite reed chamber end 100 and are spaced from both ends 99 and 100 of reed chamber 102. Air Outlet 112 is spaced from end 100 of reed housing 20 and reed supporting surfaces 108. Catheter 22 is attached to air outlet 112.

Reed 98 is supported on reed supporting surfaces 108 and pressurized air flowing into reed chamber 20 through duct 104 flows past reed 98 and out outlet 112 causing reed 98 to vibrate. Supported in this manner, reed 98 and reed support 106 define a reed space 114 therebetween. In the specific embodiment illustrated, reed 98 is of an elastomeric material. Reed 98 is positioned on reed supporting surfaces 108 and is stretched over reed supporting surfaces 108 and held in place by band 116. So held, reed 98 is in tension. The tension of reed 98 can be varied to vary the pitch of reed 98 when vibrating. In all preferred embodiments, the vibration of reed 98 should be adjustable from about 120 cycles per second to about 260 cycles per second. In other embodiments, reed 98 can take the form of a plastic or metal tongue which is secured to the reed supporting surfaces and suspended over outlet 112.

Catheter 22 has a proximal reed end 94 and a distal pharyngeal end 96. Catheter 22 directs the audibly vibrating air from reed 98 into the pharynx of the user. Catheter 22 is inserted in the specific embodiment illustrated through a nostril of the patient into the region of the pharynx such that the patient is able by means of mouth movements to articulate audible speech. Catheter 22 has sidewalls of sufficient strength such that no wall collapse occurs in operation. In a specific embodiment, catheter 22 has sidewalls of sufficient strength such that no wall collapse occurs when the catheter is bent into a radius of about one-half inch, respectively.

Catheter 22 between proximal end 94 and pharyngeal end 96 is from about 12 inches to about 14 inches long. In addition to the opening 118 in pharyngeal end 96 of catheter 22, catheter 22 has a plurality of fenestrations 120. Fenestrations 120 are of a size and number to prevent pressures in excess of that causing individuals to gag when pharyngeal end 96 is positioned within the pharynx of the user or reed 98 to stop vibrating to build up in catheter 22. In a specific embodiment, catheter 22 has three fenestrations 120 in addition to opening 118 therein formed adjacent to pharyngeal end 96 of catheter 22.

When catheter 22 is correctly positioned within the pharynx of the user, pharyngeal end 96 is positioned to about the level of the uvula. Positioning pharyngeal end 96 significantly below the uvula will cause the user to gag. Positioning pharyngeal end 96 above the uvula either results in no audibly articulate speech or speech which has preferably, end 96 should be within about a centimeter of the uvula.

Catheter 22 may be No. 8, 10, 12 or 14 French (Fr) catheters. In a specific embodiment, catheter 22 is of silastic or latex material. No. 8 French catheters are preferred. No. 14 french catheters can be used but are not as comfortable and may give the user a burning sensation when positioned in a nostril and pharynx of the user. Preferably the catheter is positioned in a nostril. While catheter 22 can be also positioned in the mouth, catheter 22 may obstruct during speech articulation; and thus, the positioning of catheter 22 in the nostril is preferred.

In all embodiments of the invention, regulator 14, tubing 18, reed housing 20, and catheter 22 combine to deliver to reed 98 air at a sufficient pressure and flow rate to vibrate the reed from about 256 cycles per second to about 130 cycles per second. Regulator 14, tubing 18, reed chamber 20 and catheter 22 in combination also deliver to the distal pharyngeal end 96 of catheter 22 air at a sufficient air pressure and flow rate to enable the user to articulate audibly comprehensible speech when catheter 22 is positioned in the pharynx as afore mentioned, but at a flow rate and air pressure less than that causing the individual to gag or to stop reed 98 from vibrating. This is accomplished by providing pharyngeal end 96 with fenestrations of sufficient size and number and choosing the length and inside diameter of catheter 22 and tubing 18 and the inside dimensions of reed chamber appropriately to result in the proper pressure and flow rate at pharyngeal end 96 at a desired setting of regulator 14.

The flow of air from compressed air source 12 to regulator 14 is controlled by means of air valve 16. Air valve 16 is an electro-mechanical valve operable in response to a power supply actuated by a patient operated electrical switch. In a specific embodiment, the patient operated switch 32 is manually operable single pole single throw control switch such as the traditional kind of patient can switch used in most hospitals.

Air valve 16 operates in response to power supply 24. Power is furnished to power supply 24 through grounded plug 26 which is connected to any conventional 117 volt 60 cycle AC source. Power from grounded plug 26 is conducted by line cord 28 to power supply 24 and is fused on one lead thereof by means of fuse 30. Single pole single throw switch 32 controls the application of power through fuse 30 to stepdown transformer 36 which in the embodiment shown has a secondary output of approximately 24 volts AC. Secondary output of stepdown transformer 36 is applied to full waive rectifier bridge 38 comprising diodes 40, 42, 44 and 46. Alternately, a battery pack can be utilized in lieu of the AC source and stepdown transformer 36 for portable use.

The rectified output of full wave rectifier bridge 38 is applied to a voltage divider network comprising resistor 48 and resistor 50. The power on indicator 56 is connected in parallel with resistor 50 to indicate the closure of single pole single throw switch 32 through the application of power to stepdown transformer 36.

The second voltage divider network comprising series connected resistor 52 and resistor 54 is connected in parallel to the voltage divider network comprising resistor 48 and resistor 50 through switch jack 60. Switch jack 60 allows the application of power to the series connected resistors 52 and 54 by means of the closure of the single pole single throw switch 32. When electrical contact is made across the terminals of switch jack 60, the output of full wave rectifier bridge 38 is applied across resistor 52 and resistor 54 thereby illuminating valve open indicator 58 and energizing relay coil 62. When energized, relay coil 62 causes the closing of relay contacts 34 in the primary circuit of stepdown transformer 36. When a switch connected to switch jack 60 is in the closed position, relay contacts 34 close and power is applied to solenoid coil 64 thereby opening air valve 16 and allowing air to pass from compressed air source 12 to regulator 14. When not energized, solenoid coil 64 allows air valve 16 to close thereby stopping the flow of air from compressed air source 12 to regulator 14.

Upon the opening and closing of air valve 16, air is supplied to regulator 14 and air moves through tubing 18, reed chamber 102 and catheter 22. When catheter 22 positioned in the pharynx of an individual as above-described, a sudden surge of air upon the opening of air valve 16 will cause the patient to gag as the flow of air through catheter 22 is at a flow rate or pressure higher than after flow has been maintained for some time. To minimize such sudden surges of air through catheter 22, reed chamber 102 is provided in such a size in relationship to the diameter of tubing 18 and catheter 22 so as to cause air to expand into the reed chamber 102 before passing reed 98 and into the catheter 22 thereby eliminating gagging. Reed chambers 102 larger than necessary to avoid any "sudden surge" which will cause gagging are useful with the invention; however, the delivery of audibly vibrating air to the pharynx will be delayed such that the user must anticipate speech and accordingly close switch 32.

Figure 3:
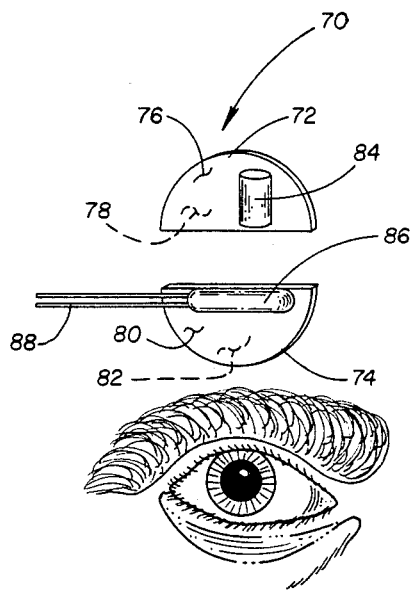
FIG. 3 is a front plan view of the auto-actuable switch of the invention in the normally open position illustrating its affixation to the forehead of a quadriplegic patient.
Figure 4:
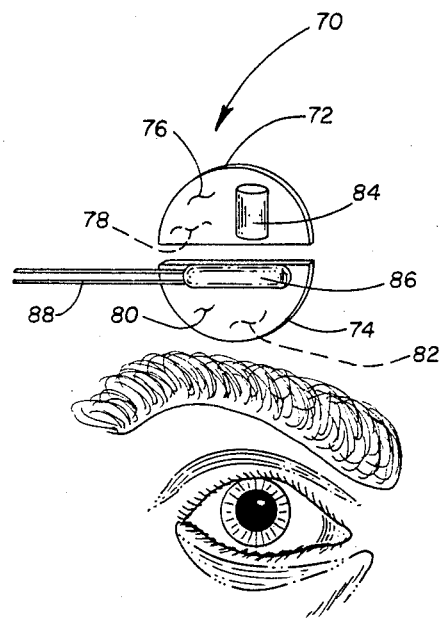
FIG. 4 is a front plan view of the specific embodiment illustrated in FIG. 3 showing the auto-actuable switch shown in FIG. 3 in the normally closed position.
Figure 6:
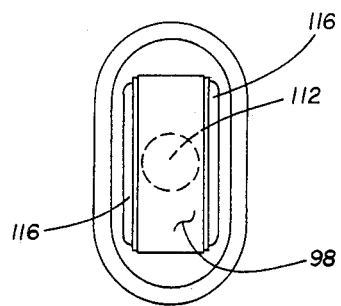
FIG. 6 is a sectional view of the tubing, reed housing and catheter shown in FIG. 1 taken substantially along Section Line 6—6 of FIG. 5.

Referring now to FIGS. 3 and 4, another embodiment 70 of switch 32 to be used with the invention is shown. Switch 70 is designed for actuation without the use of hands. Switch 70 can be used with quadriplegic patients unable to utilize manually operated switches without assistance. Switch 70 comprises an upper pad 72 and a lower pad 74. Upper pad 72 presents a front surface 76 and an adhesively coated back surface 78. Similarly, lower pad 74 presents a front surface 80 and an adhesively coated back surface 82. In use, upper pad 72 and lower pad 74 are affixed to a portion of the users anatomy over which he has voluntary muscle control by adhesively securing back surface 78 and back surface 82 to the patient. In a specific embodiment, since a quadriplegic patient or even the most severe paralyzed individuals are still able to wrinkle the forehead, upper pad 72 may be positioned over a crease line on the patients forehead with lower pad 74 positioned subjacently. Affixed to either upper pad 72 or lower 74 at the front surface 76 or 80, respectively, may be affixed a permanent magnetic 84 or other field producing device. Opposite to permanent magnet 84 on either of the counterpart lower pad 74 or upper pad 72 on the front surface 80 or 76 respectively is affixed a magnetic reed switch 86 or a corresponding field responsive switch. The output of magnetic reed switch 86 is conducted via switch leads 88 to switch jack 60 for operation of the power supply 24.

In use, upper pad 72 and lower pad 74 so positioned so that when the quadriplegic maintains his forehead in an unwrinkled condition, the magnetic reed switch 86 is unaffected by permanent magnet 84 and hence remains in an open position. Subsequently, should the quadriplegic patient wish to activate the auto actuable speech simulator 10 of the invention, the wrinkling of the forehead causes the field permanent magnet 84 to actuate magnetic switch 86 thereby closing the contact between the switch sleeves 88 and presenting a shorted condition across switch jack 60. This action introduces a vibrating air column to the tracheomized quadriplegic's pharynx and allows the quadriplegic to articulate audibly comprehensible speech.

The invention above described provides an improved speech simulator and a method for simulating speech for tracheotomized patients. The invention provides an improved auto actuable switch, speech simulator and method which allows oral communication with and readily intelligible speech by a tracheotomized patient, and even a tracheotomized quadriplegic patient. The improved speech simulator can be actuated by a hand switch if possible or by an improved forehead mounted switch by a quadriplegic and other incapacitated patients not able to use a hand switch. The improved speech simulator 10 and method of the invention provides the introduction of air through a nasal catheter and does not interfere with the patients speech, or produce unwanted noises or physical sensations during use. Speech is non-electronic and quasi natural sounding. The speech simulator and method of the invention provides a device which has few moving parts, may be simply and inexpensively produced and which requires no assistance and little, if any, instruction for use by a tracheotomized patient. The speech simulator of the invention can be used by a quadriplegic patient or even the most severely paralyzed patients and is both convenient and comfortable to use.

While there have been described above the principles of this invention in connection with specific apparatus, it is to be clearly understood that this description is made only by way of example and not as a limitation to the scope of the invention.

What is claimed is:

1. A speech simulator for a tracheotomized individual comprising
   a source of pressurized air;
   a regulator governing the pressure of said air;
   a valve responsive to actuation by said individual interconnected between said source and said regulator operable between a first position thereof wherein said air from said source is stopped and a second position thereof wherein said air passes through said valve;
   means for coupling the air source to the valve;
   means for coupling the valve to the regulator;
   a reed, a flexible tube for coupling said regulator to said reed, said reed vibrating audibly in response to the passage of said air through said valve and past said reed; and
   means for coupling said reed to the pharynx of said individual in fluid communication therewith to introduce said air flowing past said reed into the pharynx of said individual whereby said individual may articulate audibly comprehensible speech.

2. The apparatus of claim 1 wherein said source of pressurized air provides air at a pressure of between 40 to 90 P.S.I.

3. The apparatus of claim 1 wherein said regulator delivers to said reed air at a pressure and flow rate sufficient to vibrate said reed from about 260 to about 120 cycles per second.

4. The apparatus of claim 1 wherein said reed can be adjusted to vary its pitch from about 130 cycles per second to about 256 cycles per second.

5. The apparatus of claim 1 wherein the fluid coupling means includes means for transnasally coupling the pharynx to the reed to introduce said air flowing past the reed transnasally into the pharynx.

6. The apparatus of claim 5 wherein the fluid coupling means comprises a catheter having a proximal reed end coupled to the reed and a distal pharyngeal end extending into the pharynx through a nostril.

7. The apparatus of claim 6 wherein said regulator and tube delivers air to the distal pharyngeal end of said catheter at a flow rate and pressure sufficient to allow an individual to articulate audibly comprehensible speech when said end is positioned at about the uvula in the pharynx and below the flow rate and pressure causing said individual to gag.

8. The apparatus of claim 6 wherein said tube and catheter both have side walls of sufficient strength such that no side wall collapse occurs when said tubing and catheter are bent into a radius of about ½ inch, respectively.

9. The apparatus of claim 6 wherein said catheter is from about 12 inches to about 14 inches long and is from about a No. 8 French (Fr) to about a No. 14 French (Fr) catheter.

10. The apparatus of claim 6 wherein said catheter comprises a wire reinforced elastomeric tube.

11. The apparatus of claim 9 wherein said catheter adjacent to said distal end thereof has a plurality of fenestrations therein, said fenestrations being of a size and number to prevent pressures in excess of that causing individuals to gag when said distal end is adjacent to their uvula from building up in said catheter.

12. The apparatus of claim 11 wherein said catheter is of medical grade silastic or latex materials and of the group consisting of No. 8, 10, 12 and 14 French (Fr) catheters.

13. The apparatus of claim 1 wherein said valve is electromechanically operable in response to a power supply and a patient operated electrical switch.

14. The apparatus of claim 1 wherein said reed is an elastomeric membrane.

15. The apparatus of claim 1 wherein said reed comprises a thin tongue.

16. The apparatus of claim 13 wherein said electrical switch comprises a manually operable single pole single throw switch.

17. The apparatus of claim 13 wherein said electrical switch is a switch for actuation by a quadriplegic individual comprising
   first and second adhesive pads for affixation to an epidermal area of said quadriplegic individual at first spaced-apart positions, respectively, and movable towards each other to second relatively lesser spaced-apart positions, respectively, by voluntary muscular action of said quadriplegic individual,
   a field producing device secured to said first adhesive pad;
   a field responsive switch secured to said second adhesive pad and having an open condition thereof when said adhesive pads are at one of said displaced distances and a closed condition thereof when said adhesive pads are at the other of said displaced distances.

18. The apparatus of claim 17 wherein said field responsive switch comprises a magnetic reed switch.

19. The apparatus of claim 17 wherein said field producing device comprises a permanent magnet.

20. A method for simulating speech in a tracheotomized individual comprising the steps of:
   supplying a source of pressurized air;
   controlling the flow of said air between a first condition thereof wherein flow of said air is stopped and a second condition thereof wherein flow of said air is allowed in response to actuation by said individual;
   regulating the pressure of said air;

ducting said controlled air to a reed;
audibly vibrating said reed in response to the passage of said air past said reed;
introducing said air past said reed transnasally into the pharynx of said individual whereby said individual may articulate audibly comprehensible speech.

21. The method of claim 20 wherein said step of controlling the flow of said air is carried out by means of an electro-mechanically operable valve in response to a power supply actuated by a patient operated electrical switch.

22. The method of claim 20 wherein said regulator delivers to said reed at a pressure and flow rate sufficient to vibrate said reed from about 260 to about 120 cycles per second.

23. The method of claim 20 wherein said reed can be adjusted to vary its pitch from about 120 cycles per second to about 260 cycles per second.

24. The method of claim 20 wherein said regulating, vibrating and introducing steps include the step of delivering air to a catheter at a distal end adapted to be positioned in the pharynx of an individual adjacent to the uvula at a flow rate and pressure sufficient to allow an individual to articulate audibly comprehensible speech and less than that flow rate and pressure causing said individual to gag.

25. The method of claim 20 further comprising the step of
expanding said air past said reed prior to performing said introducing step whereby the abruptness of introducing air into the pharynx of an individual is minimized.

26. The method of claim 21 wherein said electrical switch is a switch for actuation by a quadriplegic individual comprising
first and second adhesive pads for affixation to an epidermal area of said quadriplegic individual at first spaced-apart positions, respectively, and movable towards each other to second relatively lesser spaced-apart positions, respectively, by voluntary muscular action of said quadriplegic individual,
a field producing device secured to said first adhesive pad;
a field responsive switch secured to said second adhesive pad and having an open condition thereof when said adhesive pads are at one of said displaced distances and a closed condition thereof when said adhesive pads are at another of said displaced distances.

27. The method of claim 21 wherein said source of pressurized air provides air at a pressure of between 40 to 90 psi.

28. The method of claim 26 wherein said field producing device comprises a permanent magnet.

29. The method of claim 26 wherein said field responsive switch comprises a magnetic reed switch.

30. A method for simulating speech in a tracheotomized individual comprising the steps of:
supplying a source of pressurized air;
controlling the flow of said air between a first condition thereof wherein flow of said air is stopped and a second condition thereof wherein flow of said air is allowed in response to actuation by said individual;
regulating the pressure of said air;
ducting said controlled air to a reed;
audibly vibrating said reed in response to the passage of said air past said reed;
introducing said air past said reed into the pharynx of said individual whereby said individual may articulate audibly comprehensible speech.

31. The method of claim 30 wherein said step of controlling the flow of said air is carried out by means of an electro-mechanically operable valve in response to a power supply actuated by a patient operated electrical switch.

32. The method of claim 30 further comprising the step of
expanding said air past said reed prior to performing said introducing step whereby the abruptness of introducing air into the pharynx of an individual is minimized.

33. The method of claim 30 wherein said regulator delivers to said reed at a pressure and flow rate sufficient to vibrate said reed from about 260 to about 120 cycles per second.

34. The method of claim 30 wherein said reed can be adjusted to vary its pitch from about 120 cycles per second to about 260 cycles per second.

35. The method of claim 30 wherein said regulating, vibrating and introducing steps include the step of delivering air to a catheter at a distal end adapted to be positioned in the pharynx of an individual adjacent to the uvula at a flow rate and pressure sufficient to allow an individual to articulate audibly comprehensible speech and less than that flow rate and pressure causing said individual to gag.

36. The method of claim 31 wherein said source of pressurized air provides air at a pressure of between 40 and 90 psi.

37. The method of claim 36 wherein said electrical switch is a switch for actuation by a quadriplegic individual comprising
first and second adhesive pads for affixation to an epidermal area of said quadriplegic individual at first spaced-apart positions, respectively, and movable towards each other to second relatively lesser spaced-apart positions, respectively, by voluntary muscular action of said quadriplegic individual,
a field producing device secured to said first adhesive pad;
a field responsive switch secured to said second adhesive pad and having an open condition thereof when said adhesive pads are at one of said displaced distances and a closed condition thereof when said adhesive pads are at another of said displaced distances.

38. The method of claim 38 wherein said field responsive switch comprises a magnetic reed switch.

39. The method of claim 38 where said field producing device comprises a permanent magnet.

40. The method of claim 38 and further including the step of affixing the first and second adhesive pads to the forehead of said quadriplegic individual.

* * * * *

UNITED STATES PATENT AND TRADEMARK OFFICE
CERTIFICATE OF CORRECTION

PATENT NO. : 4,586,931
DATED      : May 6, 1986
INVENTOR(S): Eric D. Blom; Mark I. Singer; Barry A. Harkleroad It is certified that error appears in the above-identified patent and that said Letters Patent is hereby corrected as shown below:

At column 12, line 39, delete "36" and insert therefor --31--;

At column 12, line 56, delete "38" and insert therefor --37--;

At column 12, line 58, delete "38" and insert therefor --37--; and

At column 12, line 60, delete "38" and insert therefor --37--.

Signed and Sealed this

Twenty-ninth Day of July 1986

[SEAL]

Attest:

DONALD J. QUIGG

Attesting Officer

Commissioner of Patents and Trademarks